US005750147A

United States Patent [19]
Kantor

[11] Patent Number: 5,750,147
[45] Date of Patent: May 12, 1998

[54] METHOD OF SOLUBILIZING AND ENCAPSULATING ITRACONAZOLE

[75] Inventor: Martin L. Kantor, Mamaroneck, N.Y.

[73] Assignee: Emisphere Technologies, Inc., Hawthorne, N.Y.

[21] Appl. No.: 475,887

[22] Filed: Jun. 7, 1995

[51] Int. Cl.$^6$ .............................. B01J 13/04; A61K 9/64; A61K 31/415; A01N 43/50
[52] U.S. Cl. .............................. 424/491; 264/4.1; 264/4.6; 424/435; 514/400; 514/963
[58] Field of Search .............................. 424/435, 491; 514/963, 400

[56] References Cited

U.S. PATENT DOCUMENTS

| | | |
|---|---|---|
| Re. 24,899 | 11/1960 | Green . |
| 2,671,451 | 3/1954 | Bolger .............................. 128/260 |
| 2,862,918 | 12/1958 | Meyer et al. .............................. 260/123.5 |
| 2,868,740 | 1/1959 | Luce .............................. 260/8 |
| 2,971,916 | 2/1961 | Schleicher et al. .............................. 252/62.5 |
| 3,016,308 | 1/1962 | Macaulay .............................. 177/37 |
| 3,052,655 | 9/1962 | Fox et al. .............................. 260/78 |
| 3,057,344 | 10/1962 | Abella et al. .............................. 128/2 |
| 3,076,790 | 2/1963 | Fox et al. .............................. 260/78 |
| 3,170,802 | 2/1965 | Fukushima .............................. 99/145 |

(List continued on next page.)

FOREIGN PATENT DOCUMENTS

| | | | |
|---|---|---|---|
| 1077842 | 8/1976 | Canada .............................. | A16K 9/50 |
| 0 000 667 A1 | 2/1979 | European Pat. Off. .............................. | A61K 9/50 |
| 0 036 145 A1 | 9/1981 | European Pat. Off. .............................. | A61K 31/62 |
| 0 105 804 | 4/1984 | European Pat. Off. .............................. | C12N 15/00 |
| 0 130 162 A2 | 1/1985 | European Pat. Off. .............................. | B01J 13/02 |
| 0 170 540 A1 | 2/1986 | European Pat. Off. .............................. | A61K 9/52 |
| 0 342 054 A2 | 11/1989 | European Pat. Off. .............................. | A61K 7/06 |
| 0 342 056 A2 | 11/1989 | European Pat. Off. .............................. | A61K 7/06 |
| 0 365 183 | 4/1990 | European Pat. Off. .............................. | C07O 311/21 |
| 0 366 277 | 5/1990 | European Pat. Off. .............................. | A61K 9/107 |
| 0 448 057 | 9/1991 | European Pat. Off. .............................. | C12P 21/08 |
| 0 452 161 | 10/1991 | European Pat. Off. .............................. | A61K 7/48 |
| 0 459 795 | 12/1991 | European Pat. Off. .............................. | A61K 37/02 |
| 0 467 389 | 1/1992 | European Pat. Off. .............................. | A61K 9/52 |
| 0 490 549 A1 | 6/1992 | European Pat. Off. .............................. | A61K 47/12 |
| 0 517 211 A1 | 9/1992 | European Pat. Off. .............................. | A61K 47/12 |
| 0 616 799 A1 | 9/1994 | European Pat. Off. .............................. | A61K 7/00 |
| 1 351 358 | 3/1964 | France . | |

(List continued on next page.)

OTHER PUBLICATIONS

*Chemical Abstracts*, 76(14):72994u, (1971).
*Chemical Abstracts*, 84(7):44660d, (1975).
*Chemical Abstracts*, 86(16):107529g, (1976).
*Chemical Abstracts*, 112(15):134663h, (1989).
*Chemical Abstracts*, 114(22):214519x, (1990).
J. Györe et al., Thermal Analysis, vol. 2 –Proceeding Fourth ICTA Budapest 1974, pp. 387–394.
*Chemical Abstracts*, 99(19) 158832b, (1982).
Derwent Abstracts, JP 67008622, (1967).

Airaudo, C.B. et al. (1987) *Journal of Food Science*, vol. 52(6), pp. 1750–1752.
Andini, S. et al. (1975) *Origins of Life*, vol. 6, pp. 147–153.
Brooke, S. 1 et al. (1977) *BioSystems*, vol. 9, pp. 1–22.
Chen et al. (1975) "Evidence for Hemiacetal Formation", *Biochemistry*, vol. 18, No. 5, pp. 921–925.
Davis et al. (1983) "Leucinal Inhibits . . . ", *Pharmacology Biochemistry Behavior*, vol. 19, pp. 791–794.
Dose, K. (1974) *Origins of Life*, vol. 5, pp. 239–252.
Fasman et al. (1964) *Biochemistry*, vol. 3, No. 11, pp. 1665–1674.
Fox, S.W. et al. (1976) *BioSystems*, vol. 8, pp. 40–44.
Fox, S.W. et al., *Molecular Evolution and the Origin of Life*, Maxel Decker, New York (1977).
Fox, S.W. et al. (1968) *Biochim. Biophys. Acta*, vol. 160, pp. 246–249.
Fox, S.W. (1976) *Origins of Life*, vol. 7, pp. 49–68.
Fox, S.W. (1980) *Naturwissenschaften*, vol. 67, pp. 378–383.
Fox, S.W. et al. (1960) *Archives of Biochemistry and Biophysics*, vol. 86, pp. 281–285.
Fox, S.W. et al. (1974) *Origins of Life*, vol. 5, pp. 227–237.
Fox, S.W. (1984) *Origins of Life*, vol. 14, pp. 485–488.
Gol'dovskii, A.M. (1978) *Zhurnal Evolyutsionnoi Biokhimii i Fiziologii*, vol. 14(6), pp. 437–439.
Gurrieri, S. et al. (1973) *Thermochimica Acta*, vol. 7, pp. 231–239.
Harada, K. et al. (1979) *BioSystems*, vol. 11, pp. 47–53.
Harada, K. et al., (1960) *Archives of Biochemistry and Biophysics*, vol. 86, pp. 274–280.
Hare (1970) *Etude Cenetique De La Polycondensation Thermique D'χ-Amino Acides*, vol. 45, pp. 330–339.
Heinrich, M.R. et al. (1969) *Archives of Biochemistry and Biophysics*, vol. 130, pp. 441–448.
Heinz, B. et al. (1981) *BioSystems*, vol. 14, pp. 33–40.
Hennon, G. et al. (1975) *Biochimie*, vol. 57, pp. 1395–1396.
Hsu, L.L. et al. (1976) *BioSystems*, vol. 8, pp. 89–101.
Hsu, L.L. et al. (1971) *Currents in Modern Biology*, vol. 4, pp. 12–25.
Ishima, Y. et al. (1981), *BioSystems*, vol. 14, pp. 243–251.
Jackson et al. (1991) "Pharmacological . . . ", *J. Pharm. & Exp. Thera.*, vol. 261, No. 1, pp. 546–552.
Jungck, J.R. et al. (1973) *Naturwissenschaften*, vol. 60, pp. 425–427.
Kokufuta, E. et al., (1984) *BioSystems*, vol. 16, pp. 175–181.
Krampitz, G. et al. (1967) *Naturwissenschaften*, pp. 516–517.
Krampitz, G. et al. (1968) *Naturwissenschaften*, pp. 345–346.
Krampitz, G. et al. (1966) *Naturwissenschaften*, pp. 7 and 8.
Lacey, Jr., J.C. et al. (1979) *BioSystems*, vol. 11, pp. 9–17.

(List continued on next page.)

Primary Examiner—Richard D. Lovering
Attorney, Agent, or Firm—Darby & Darby

[57] ABSTRACT

Methods for preparing microspheres containing imidazole derivatives are provided. Also provided is the use of imidazole derivatives containing microspheres for treating fungal infections. Oral dosage forms for oral administration are also provided.

4 Claims, 4 Drawing Sheets

U.S. PATENT DOCUMENTS

| | | | |
|---|---|---|---|
| 3,190,837 | 6/1965 | Brynko et al. | 252/316 |
| 3,474,777 | 10/1969 | Figge et al. | 128/2 |
| 3,491,093 | 1/1970 | Pachter et al. | 260/247.5 |
| 3,565,559 | 2/1971 | Sato et al. | 424/37 |
| 3,567,650 | 3/1971 | Bakan | 252/316 |
| 3,574,832 | 4/1971 | Engel et al. | 424/183 |
| 3,576,758 | 4/1971 | Emrick | 252/316 |
| 3,687,926 | 8/1972 | Arima et al. | 530/329 |
| 3,725,113 | 4/1973 | Chang | 117/82 |
| 3,794,561 | 2/1974 | Matsukawa et al. | 195/29 R |
| 3,795,739 | 3/1974 | Birkmayer et al. | 424/274 |
| 3,822,348 | 7/1974 | Higashi et al. | 424/95 |
| 3,849,550 | 11/1974 | Teitelbaum | 424/78 |
| 3,937,668 | 2/1976 | Zolle | 252/316 |
| 3,939,253 | 2/1976 | Bodor et al. | 424/309 |
| 3,956,172 | 5/1976 | Saeki et al. | 252/316 |
| 3,962,416 | 6/1976 | Katzen | 424/19 |
| 4,035,507 | 7/1977 | Bodor et al. | 424/311 |
| 4,048,268 | 9/1977 | Ludwig | 264/15 |
| 4,061,466 | 12/1977 | Sjoholm et al. | 23/230 B |
| 4,117,801 | 10/1978 | Dannelly et al. | 118/20 |
| 4,147,767 | 4/1979 | Yapel | 424/22 |
| 4,183,849 | 1/1980 | Hansen et al. | 260/112.7 |
| 4,199,561 | 4/1980 | Roth et al. | 424/32 |
| 4,217,370 | 8/1980 | Rawlings et al. | 426/98 |
| 4,272,506 | 6/1981 | Schwarzberg | 424/8 |
| 4,345,588 | 8/1982 | Widder et al. | 128/1.3 |
| 4,348,384 | 9/1982 | Horikoshi et al. | 424/101 |
| 4,351,337 | 9/1982 | Sidman | 128/260 |
| 4,352,993 | 10/1982 | Lim | 435/178 |
| 4,357,259 | 11/1982 | Senyei et al. | 252/316 |
| 4,388,304 | 6/1983 | Nyeki et al. | 424/177 |
| 4,402,856 | 9/1983 | Schnoring et al. | 428/402.22 |
| 4,405,598 | 9/1983 | Brown | 424/45 |
| 4,442,090 | 4/1984 | Kakeya et al. | 424/178 |
| 4,446,138 | 5/1984 | Pack | 424/248.57 |
| 4,450,150 | 5/1984 | Sidman | 424/1.1 |
| 4,457,907 | 7/1984 | Porter | 424/10.3 |
| 4,460,563 | 7/1984 | Calanchi | 424/35 |
| 4,462,839 | 7/1984 | McGinley et al. | 106/198 |
| 4,462,991 | 7/1984 | Higuchi et al. | 424/177 |
| 4,473,620 | 9/1984 | Wu et al. | 428/402.24 |
| 4,483,807 | 11/1984 | Asano et al. | 264/22 |
| 4,492,684 | 1/1985 | Goosen et al. | 424/19 |
| 4,518,433 | 5/1985 | McGinley et al. | 106/180 |
| 4,590,265 | 5/1986 | Bogan et al. | 536/63 |
| 4,608,278 | 8/1986 | Frank et al. | 427/213.35 |
| 4,613,500 | 9/1986 | Suzuki et al. | 429/85 |
| 4,647,455 | 3/1987 | De Bold | 424/95 |
| 4,666,641 | 5/1987 | Fickat et al. | 264/4.3 |
| 4,671,954 | 6/1987 | Goldberg | 424/450 |
| 4,673,566 | 6/1987 | Goosen et al. | 424/19 |
| 4,683,092 | 7/1987 | Tsang | 424/491 X |
| 4,703,042 | 10/1987 | Bodor | 514/56 |
| 4,708,952 | 11/1987 | Salatinjants | 514/158 |
| 4,745,161 | 5/1988 | Saudek et al. | 525/420 |
| 4,753,804 | 6/1988 | Iaccheri et al. | 424/491 |
| 4,757,007 | 7/1988 | Satoh | 435/69 |
| 4,757,024 | 7/1988 | Roper | 436/507 |
| 4,766,012 | 8/1988 | Valenti | 427/213.36 |
| 4,774,320 | 9/1988 | Tagliabue et al. | 530/328 |
| 4,789,734 | 12/1988 | Pierschbacher | 530/395 |
| 4,835,312 | 5/1989 | Itoh et al. | 564/205 |
| 4,844,904 | 7/1989 | Hamaguchi et al. | 424/450 |
| 4,873,087 | 10/1989 | Morishita et al. | 424/433 |
| 4,886,663 | 12/1989 | Houghten | 424/88 |
| 4,895,725 | 1/1990 | Kantor et al. | 424/455 |
| 4,897,444 | 1/1990 | Brynes et al. | 525/54.1 |
| 4,900,730 | 2/1990 | Miyauchi | 514/12 |
| 4,925,673 | 5/1990 | Steiner | 424/455 |
| 4,963,364 | 10/1990 | Fox et al. | 424/455 |
| 4,976,968 | 12/1990 | Steiner | 424/491 |
| 4,983,402 | 1/1991 | Steiner | 424/491 |
| 4,996,292 | 2/1991 | Fox et al. | 528/328 |
| 5,039,481 | 8/1991 | Pacifici et al. | 422/4 |
| 5,055,300 | 10/1991 | Gupta | 424/409 |
| 5,066,487 | 11/1991 | Morelle et al. | 424/68 |
| 5,069,936 | 12/1991 | Yen | 427/213.33 |
| 5,077,278 | 12/1991 | Hafner et al. | 514/30 |
| 5,100,669 | 3/1992 | Hyon et al. | 424/426 |
| 5,186,947 | 2/1993 | Goettsche et al. | 424/638 |
| 5,204,099 | 4/1993 | Barbier et al. | 424/401 |
| 5,206,384 | 4/1993 | Shibahara et al. | 548/537 |
| 5,250,236 | 10/1993 | Gasco | 264/4.4 |
| 5,271,961 | 12/1993 | Mathiowitz et al. | 427/213.31 |
| 5,328,992 | 7/1994 | Peter et al. | 534/116 |
| 5,384,133 | 1/1995 | Boyes et al. | 424/501 |
| 5,418,010 | 5/1995 | Janda et al. | 427/213.31 |
| 5,474,997 | 12/1995 | Gray et al. | 514/252 |
| 5,536,813 | 7/1996 | Charpenel et al. | 530/324 |

FOREIGN PATENT DOCUMENTS

| | | | |
|---|---|---|---|
| 1 468 601 | 2/1967 | France . | |
| 2 133 926 | 12/1972 | France | A61K 27/00 |
| 2 326 934 | 5/1977 | France | A61K 47/00 |
| 2 565 102 | 12/1985 | France | A61K 9/52 |
| 2 424 169 | 12/1974 | Germany | A61K 9/00 |
| 3 202 255 | 10/1982 | Germany | C08L 89/00 |
| 3 612 102.9 | 10/1986 | Germany | C07K 15/00 |
| 71258/2 | 12/1987 | Israel . | |
| 48-24246 | 3/1973 | Japan . | |
| 56-68612 | 6/1981 | Japan | A61K 31/19 |
| 58-35111 | 3/1983 | Japan | A61K 9/66 |
| 280825 | 12/1964 | Netherlands . | |
| 280826 | 12/1964 | Netherlands . | |
| B-146698 | 11/1982 | Norway | A61K 37/26 |
| 929401 | 6/1963 | United Kingdom . | |
| 1236885 | 9/1969 | United Kingdom . | |
| 1 567 763 | 5/1980 | United Kingdom | A61K 9/22 |
| WO 85/00105 | 1/1985 | WIPO | A61K 9/52 |
| WO85/00110 | 1/1985 | WIPO | A61K 47/00 |
| WO 85/02772 | 7/1985 | WIPO | A61K 49/00 |
| WO 87/04076 | 7/1987 | WIPO | A61K 45/02 |
| WO 88/01213 | 2/1988 | WIPO | B23B 5/16 |
| WO 92/19263 | 12/1992 | WIPO | A61K 39/00 |
| WO 93/18754 | 9/1993 | WIPO | A61K 9/16 |
| WO 93/25583 | 12/1993 | WIPO | C07K 15/00 |
| WO 94/14420 | 7/1994 | WIPO | A61K 9/16 |
| WO 94/18950 | 9/1994 | WIPO | A61K 9/127 |
| WO 94/18997 | 9/1994 | WIPO | A61K 37/00 |
| WO 94/21234 | 9/1994 | WIPO | A61K 7/00 |
| WO 94/23702 | 10/1994 | WIPO | A61K 9/16 |
| WO 94/23767 | 10/1994 | WIPO | A61L 9/16 |
| WO 94/24291 | 10/1994 | WIPO | A61K 39/015 |
| WO 94/28878 | 12/1994 | WIPO | A61K 9/14 |
| WO 95/11690 | 5/1995 | WIPO | A61K 37/00 |

OTHER PUBLICATIONS

Lacey, Jr., J.C. et al. (1979) *BioSystems*, vol. 11, pp. 1–7.

Martinez Luque–Romero, M. et al. (1986) *BioSystems* vol. 19, pp. 267–272.

Masinovsky, Z. et al. (1989) *BioSystems*, vol. 22, pp. 305–310.

Matsuno, K. (1982) *BioSystems*, vol. 15, pp. 1–11.

Matsuno, K. (1984) *BioSystems*, vol. 17, pp. 11–14.

Matsuno, K. (1981) *BioSystems*, vol. 14, pp. 163–170.

McAlhaney, W.W. et al. (1976) *BioSystems*, vol. 8, pp. 45–50.

Melius, P. et al. (1987) *BioSystems*, vol. 20, pp. 213–217.

Melius, P. et al. (1975) *Bioorganic Chemistry*, vol. 4, pp. 385–391.

Melius, P. (1979) *BioSystems*, vol. 11, pp. 125–132.

Miquel, J. et al. (1971) *Currents in Modern Biology*, vol. 3, pp. 299–306.

Nakashima, T. et al. (1980) *J. Mol. Evol.*, vol. 15, pp. 161–168.

Nakashima, T. et al. (1981) *BioSystems*, vol. 14, pp. 151–161.

Novak, V.J.A. (1984) *Origins of Life*, vol 14, pp. 513–522.

Olafsson, P.G. et al. (1971) *Polymer Letters*, vol. 9, pp. 521–528.

Phillips, R.D. et al. (1974) *Int. J. Peptide Protein Res.*, vol. 6, pp. 309–319.

Przybylski, A.T. et al. (1982) *Die Naturwissenschaften*, vol. 69, pp. 561–563.

Przybylski, A.T. et al. (1984) *Applied Biochemistry and Biotechnology*, vol. 10, pp. 301–307.

Przybylski, A.T. (1985) *BioSystems*, vol. 17, pp. 281–288.

Rohlfing, D.L. (1975) *Origins of Life*, vol. 6, pp. 203–209.

Rohlfing, D.L. (1970) *Science*, vol. 169, pp. 998–1000.

Rohlfing, D.L. (1967) *Archives of Biochemistry and Biophysics*, vol. 118, pp. 468–474.

Rohlfing, D.L. et al. *Catalytic Activities of Thermal Polyanhydro–α–Amino Acids*, pp. 373–418 (1969).

Rohlfing, D.L. et al. (1976) *BioSystems*, vol. 8, pp. 139–145.

Ryan, J.W. et al. (1973) *BioSystems*, vol. 5, pp. 115–118.

Saunders, M.A. et al. (1974) *BioSystems*, vol. 6, pp. 81–92.

Snyder, W.D. et al. (1975) *BioSystems*, vol. 7, pp. 222–229.

Sokol, P.E. (1974) *Journal of the American Oil Chemists' Society*, vol. 52, pp. 101–102.

Tschager et al. (1988) *Milchwirtschaftliche Berichte*, vol. 95, pp. 79–83.

Vaughan, G. et al. (1987) *BioSystems*, vol. 20, pp. 219–223.

Vol'kenshtein, M.V. (1989) *Molekulyarnaya Biologiya*, vol. 23(1), pp. 23–37.

Waehneldt, T.V. et al. (1968) *Biochim. Biophys. Acta*, vol. 160, pp. 239–245.

Williams et al. (1991) *J. Biol. Chem.*, vol. 266, No. 8, pp. 5182–5190.

Yuki, A. et al. (1969) *Biochemical and Biophysical Research Communications*, vol. 36(4), pp. 657–663.

Zulaski et al. (1983) "New Carboxyalkyl Inhibitors of Brain Enkenphalinase", *J. Med. Chem.*, 26, pp. 60–65.

(1986) *Chemical Abstracts*, vol. No. 105(1), Abstract No. 12027p.

(1985) *Chemical Abstracts*, vol. No. 102(6), Abstract No. 50870d.

Chemical Abstract, vol. 80(9) Abst. No. 52392a (1974).

Bergeron, Raymond J., et al. (1994) "Macromolecular Self-Assembly of Diketopiperazine Tetrapeptides", *Journal of the American Chemical Society*, vol. 116, pp. 8479–8484.

Bergeron, Raymond J., et al. (1993) "A Comparative Study of the Iron–Clearing Properties of Desferrithiocin Analogues With Desferrioxamine B in a Cebus Monkey Model", *Blood*, vol. 81, No. 8, pp. 2166–2173.

Bergeron, Raymond J., et al. (1992) "A Comparison of the Iron–Clearing Properties of 1,2–Dimethyl–3–Hydroxypyrid–4–One, 1,2–Diethyl–3–Hydroxypyrid–4–One, and Deferoxamine", *Blood*, vol. 79, No. 7, pp. 1882–1890.

Bergeron, Raymond J., et al. (1991) "Evaluation of Desferrithiocin and Its Synthetic Analogs as Orally Effective Iron Chelators", *Journal of Medicinal Chemistry*, vol. 34, No. 7, pp. 2072–2078.

Bergeron, Raymond et al., "A Comparative Evaluation of Iron Clearance Models", *Annals New York Academy of Sciences*, pp. 378–393. (Mar. 13–15, 1990).

Andriuoli, G. et al. (1990), *Haemostasis* 20 (suppl. 1):154–158.

Caramazza, I., et al. (1991), *Thrombosis Research* 62:785–789.

Guarini, S. et al. (1983), *Experimentia* 41:350–352.

Guarini, S., et al. (1985), *Pharmacologial Research Communications* 17(8):685–697.

Dal Pozzo, A., et al. (1989), *Thrombosis Research* 56:119–124.

Airaudo, C.B., et al. (1987), *Journal of Food Science* 52(6):1750–1752.

Gelb, R., et al. (1983), *Lite Sciences* 33(1):83–85.

Watterberg et al. (1988), *Pediatric Research*, vol. 23, No. 4, part 2, pp. 570A, column 1, abstract No. 2209.

Berstein (1985), *Chest* 87(1):68S–73S.

Damage et al. (1988), *Diabetes* 37:246–251.

184358, *Chemical Abstracts*:83 (1975).

Amino, Y., et al., *Chem. Pharm. Bull.* 36(11):4426–4434 (1988).

Baughman, R.A. et al., *Proc. of the 6th Inter'l. Symp. on Recent Advs. in Drug Delivery Systems, Ctr. for Controlled Chem. Delivery, University of Utah*, Feb. 22–25, 1993, Salt Lake City, UT, pp. 179–180 "Method for Assessing The Stability of Proteinoid Microspheres".

Haas, S. et al., "Assessment of Stability Of Proteinoid Microspheres", *Proceed Intern. Symp. Control. Rel. Bioact. Mater.*, 20 (1993), Controlled Release Society, Inc.

X. Ma, et al., *Proceed. Intern. Symp. Control. Rel. Bioact. Mater.*, 20 (1993), Controlled Release Society, Inc. "In Vitro Mechanistic Investigation of the Proteinoid Microsphere Oral Delivery System".

Yen, H.–R H., et al., "Adsorption of Sulforhodamine 101 on Proteinoid Microspheres" *Proceed. Intern. Symp. Control. Rel. Bioact. Mater.*, 20 (1993), Controlled Release Society, Inc.

Presented at "*IBC Rational Drug Design Conference*", San Diego, Calif. –Dec. 1994.

Bergeron, Raymond J. et al., *J. Am. Chem. Soc.* 1994, 116,8479–8484 "Macromolecular Self–Assembly of Diketopiperazine Tetrapeptides".

Leone–Bay et al., Presented at "*Winter Conference on Medicinal and Bioorganic Chemistry*" Steamboat Springs, Colorado –Feb. 1995 Microsphere Formation and Drug Delivery in a Series of Derivatized Amino Acids.

Santiago et al., *Pharm. Res.* 11: 1994, pp. S–298 "Oral Delivery of Heparin Microspheres made with Modified Amino Acids".

Leone–Bay et al., *Pharm. Res.* 11: 1994, p. S–121 "Oral Delivery of Heparin using Acylated Amino Acids".

Sarubbi et al., *Pharm. Res.* 11: 1994, p. S–299 "Oral Calcitonin Delivery using the PODDS Technology".

Leipold et al., *Pharm. Res.* 11: 1994, p. S–298 "Oral Delivery of Interferon in Rats and Primates".

Santiago et al., *Pharm. Res.* 11: 1994, p. S–298 "Evaluation in Rats of Vehicles for the Oral Delivery of Low Molecular Weight Heparin".

X. Ma et al., PDD 7303 *Pharmaceutical Research* 9(10):S–244, 1992 (Oct. Supplement).

Milstein et al., *Symposia Abstracts*. AAPS Annual Meeting, San Antonia, TX, Nov. 15–19, 1993.

Santiago et al. "Initial Studies In The Assessment of Proteinoid Microsphere Activity" *Proceed. Inter. Symp. Control. Rel. Bioact. Mater.*, 20 (1993), Controlled Release Society, Inc.

Santiago et al. "Oral Immunization of Rats with Influenza Virus M Protein (M1) Microspheres" *Proceed. Intern. Symp. Control. Rel. Bioact. Mater.*, 19 (1992), Controlled Release Society, Inc., pp. 116–117.

Santiago et al. "Proteinoid Microspheres For The Oral Delivery of Heparin" *Proceed. Intern. Symp. Control. Rel. Bioact. Mater.*, 19 (1992), Controlled Release Society, Inc. pp. 514–515.

Santiago et al. *American Society for Microbiology* 92nd General Meeting, Abstract of the General Meeting, p. 159, May 26–30, 1992.

Milstein et al. "Preparation And In Vitro Characterization Of Proteinoid Microspheres" *Proceed Intern. Symp. Control. Rel. Bioact. Mater.*, 19 (1992), Controlled Release Society, Inc. pp. 516–517.

Doris K. Chiappetta, *Eastern Analytical Symposium*, Nov. 17, 1992 "Solutions for Problems in Bioanalysis".

Elizabeth A. Harris. M.S., *Eastern Analytical Symposium* Nov. 17, 1992 "Solutions for Problems in Bioanalysis".

*AAPS 6th Ann. Meeting and Expo.*,"Proteinoids —A Novel Drug Delivery System" Nov. 19, 1992, p. 33.

Milstein et al., "Efficient Oral Delivery Of Monoclonal Antibodies By Proteinoid Encapsulation" *The 1993 Miami Bio/Technology Winter Symposium —Advances in Gene Technology: Protein Engineering and Beyond*, Jan. 17–22, 1993.

Xinghang Ma, et al. "Stability Study of Drug–loaded Proteinoid Microsphere Formulations during Freeze–drying" *Journal of Drug Targeting*, 1994, vol. 2, pp. 9–21.

Baughman et al. "Screening Candidate Microsphere Formulations By Incubating In Simulated Digestive Fluids" *Proc. of the 6th Intern'l Sympo., on Recent Advances in Drug Delivery Systems*, Ctr. for Controlled Chem. Delivery, University of Utah, Feb. 22–25, 1993, pp. 181–182.

Franssen et al., J. Med. Chem., 35:1246–1259, 1992.

Kondo:*Microcapsule Processing and Technology*, Chap. 15 "Microencapsulation By Spray–Drying Process", Marcel–Dekker, Inc., New York (1979), pp. 154–165.

FIG. IC
FIG. ID
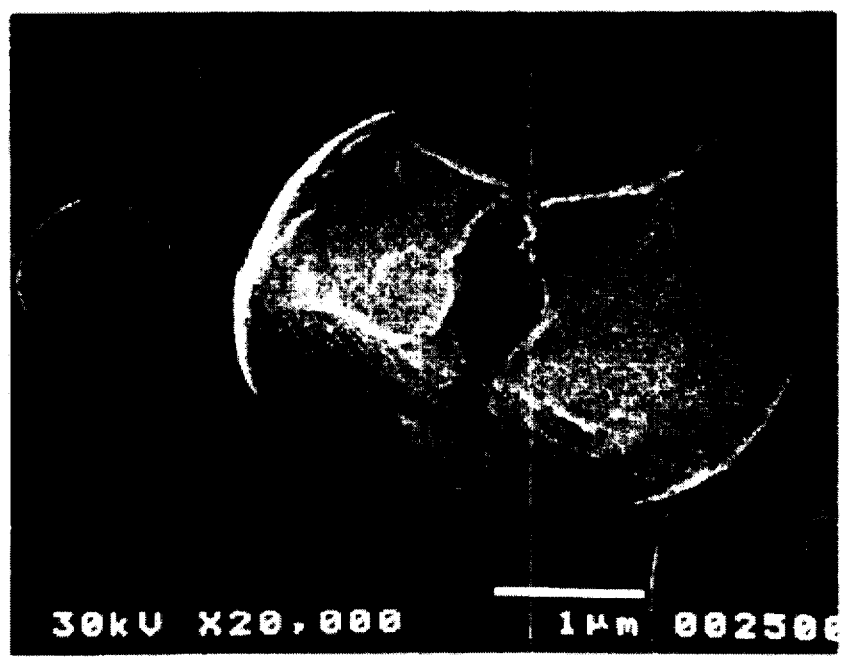

FIG. IE
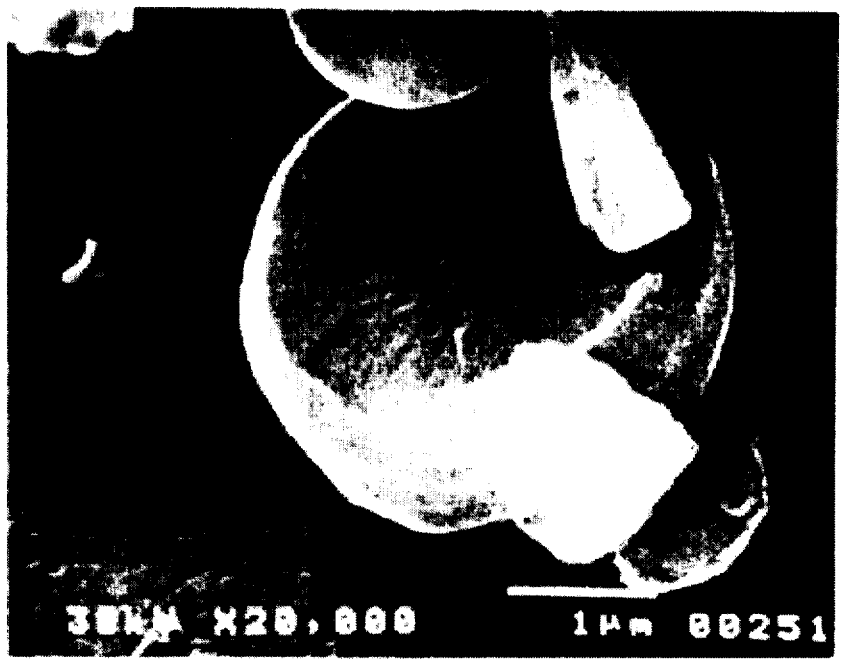
FIG. IF
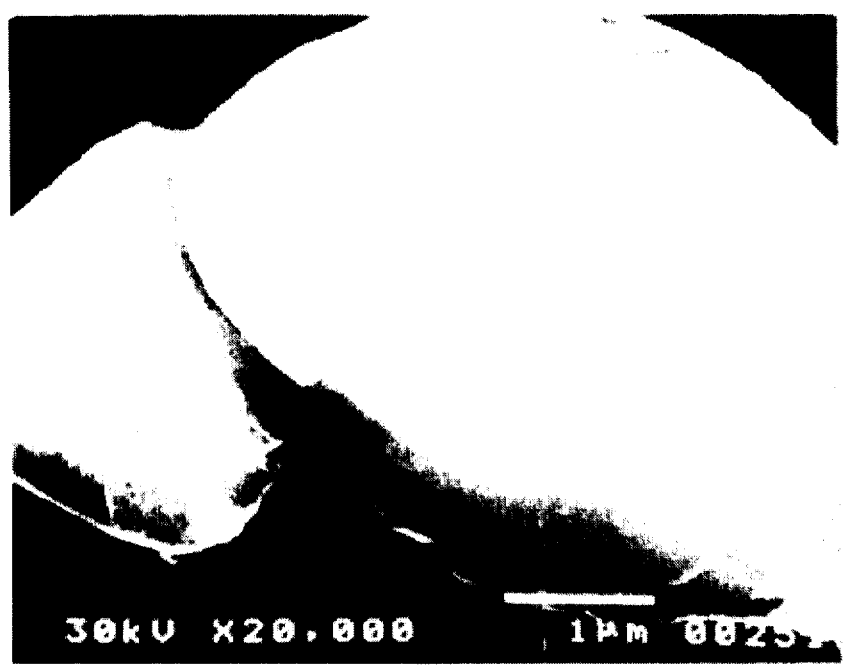

METHOD OF SOLUBILIZING AND ENCAPSULATING ITRACONAZOLE

FIELD OF THE INVENTION

The present invention relates to the preparation of solutions containing imidazole derivatives and to the use of those solutions in the preparation of microspheres. The imidazole derivative containing microspheres are effective in treating fungal infections, particularly in mammals. The microspheres facilitate the oral administration of relatively large amounts of the imidazole derivative, with increased bioavailability.

BACKGROUND OF THE INVENTION

Many present systems for delivering active agents to targets are severely limited by biological, chemical, and physical barriers, which are imposed by the environment through which delivery occurs, the environment of the target itself, or the target itself. Delivery is also limited, in many instances, by the chemical nature of the active agent. For example, oral delivery is generally ineffective with active agents that are poorly water-soluble.

The imidazole derivative family of compounds is particularly effective against a broad range of fungal infections such as those caused by *Trichophyton rubrum*, *Tricophyton mentagrophytes*, *Epidermophyton floccsum*, and *Candida albicans*, but these compounds are either partially water soluble or insoluble in water. For example, the solubility of itraconazole in water is less than 0.00001 g/ml.

Partially because imidazole derivatives are typically insoluble in water, they are difficult to administer orally. Consequently although imidazole derivatives are frequently prescribed for the treatment of fungal infections, they have been available only in topical preparations or in oral formulations with limited bioavailability.

In recent years, fungal infections, such as those caused by *Candida albicans* in particular have become more prevalent and intractable due to their appearance in immunocompromised patients, such as those infected with Human Immunodeficiency Virus (HIV) or those suffering from Acquired Immunodeficiency Syndrome (AIDS).

For example, U.S. Pat. No. 3,717,655 discloses imidazole derivatives which have antifungal and antibacterial activity. These compounds are almost insoluble in aqueous solutions such as water and are very poorly soluble in polar solvents such as ethanol.

Das et al., U.S. Pat. No. 4,912,124, disclose a solvent system for imidazole derivatives that include mixtures of a polar solvent, a polyhydric alcohol that acts as a solubilizing agent, a nonionic or amphoteric surfactant, and a cosmetic humectant. Solutions containing at least 1 percent by weight of the imidazole derivatives can be formulated using this solvent system. However, these formulations are suitable for external topical use only.

Accordingly, there is a need for orally deliverable forms of imidazole derivative antifungal agents.

SUMMARY OF THE INVENTION

The present invention provides solutions comprising:
(a) at least about 2.5 parts by weight, based upon 100 parts by weight of solution, of a solute having the formula wherein R, $R^1$, and $R^2$ are independently hydrogen or lower alkyl;
$R^3$ is hydrogen, methyl or ethyl;

$R^4$ is hydrogen or methyl
Ar is phenyl, monohalophenyl, dihalophenyl, trihalophenyl, mono(lower alkyl)phenyl, di(lower alkyl)phenyl, lower alkoxyphenyl, or halothienyl;
$Ar^1$ is phenyl, monohalophenyl, dihalophenyl, trihalophenyl, mono(lower alkyl)phenyl, di(lower alkyl)phenyl, lower alkoxyphenyl, or cyanophenyl; and
n is 1 or 2; and
(b) a solubilizing effective amount of a solvent comprising at least one volatile organic acid solvent.

Imidazole derivative microspheres are also provided. These microspheres comprise:
(a) an imidazole derivative active agent having the formula

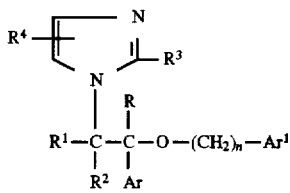

wherein R, $R^1$, and $R^2$ are independently hydrogen or lower alkyl;
$R^3$ is hydrogen, methyl or ethyl;
$R^4$ is hydrogen or methyl
Ar is phenyl, monohalophenyl, dihalophenyl, trihalophenyl, mono(lower alkyl)phenyl, di(lower alkyl)phenyl, lower alkoxyphenyl, or halothienyl;
$Ar^1$ is phenyl, monohalophenyl, dihalophenyl, trihalophenyl, mono(lower alkyl)phenyl, di(lower alkyl)phenyl, lower alkoxyphenyl, or cyanophenyl; and
n is 1 or 2; and
(b) a microsphere forming carrier selected from the group consisting of
  (i) a proteinoid;
  (ii) an acylated amino acid, poly amino acid, or a salt thereof;
  (iii) an sulfonated amino acid, poly amino acid, or a salt thereof;
  (iv) a protein or a salt thereof;
  (v) an enteric coating material; or
  (vi) any combination thereof.

Also contemplated by the present invention is a method for preparing these microspheres. The method comprises:
(A) nebulizing a solution comprising
  (a) an imidazole active agent having the formula

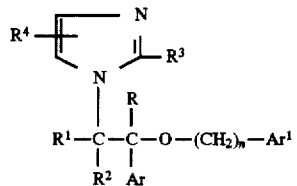

wherein R, $R^1$, and $R^2$ are independently hydrogen or lower alkyl;
$R^3$ is hydrogen, methyl or ethyl;
$R^4$ is hydrogen or methyl
Ar is phenyl, monohalophenyl, dihalophenyl, trihalophenyl, mono(lower alkyl)phenyl, di(lower alkyl)phenyl, lower alkoxyphenyl, or halothienyl;
$Ar^1$ is phenyl, monohalophenyl, dihalophenyl, trihalophenyl, mono(lower alkyl)phenyl, di(lower alkyl)phenyl, lower alkoxyphenyl, or cyanophenyl; and n is 1 or 2;

(b) an active agent and carrier solubilizing effective amount of a solvent comprising an aqueous solution of at least one volatile organic solvent; and wherein the volume:volume ratio of acid to water in said carrier solution is at least about 3:7, and (c) microsphere forming a carrier selected from the group consisting of
   (i) a proteinoid;
   (ii) an acylated amino acid or poly amino acid or a salt thereof;
   (iii) an sulfonated amino acid or poly amino acid or a salt thereof;
   (iv) a protein or a salt thereof;
   (v) an enteric coating material; or
   (vi) any combination thereof; and (B) decreasing said ratio to less than about 3:7, to yield said microspheres. Alternatively, the active agent and the carrier can be solubilized in separate solutions. The separate solutions can be nebulized together and the acid to water ratio then decreased as above.

Methods for the oral administration of imidazole derivatives are also contemplated wherein the microsphere compositions above are orally administered to an animal in need of this treatment.

BRIEF DESCRIPTION OF THE DRAWINGS cargo or active agent is distributed throughout a carrier matrix. In a solid matrix form, the carrier matrix forms a continuum in which the cargo is distributed. In the microcapsule form, the encapsulated material or cargo can be either in solution or a solid, with the carrier forming a shell around the cargo.

The methods of the present invention are cost-effective for preparing microspheres which contain imidazole derivatives, are simple to perform, and are amenable to industrial scale-up for commercial production.

Carriers

Carriers suitable for use in the present invention are microsphere forming carriers. These carriers include, without limitation, proteinoids; acylated amino acids, poly amino acids or salts thereof; sulfonated amino acids, poly amino acids or salts thereof; proteins or salts thereof, enteric coating materials; or any combination thereof.

Amino acids are the basic materials used to prepare many of the carriers useful in the present invention. Amino acids include any carboxylic acid having at least one free amino group and include naturally occurring and synthetic amino acids. The preferred amino acids for use in the present invention are ∝-amino acids and, most preferably, are naturally occurring ∝-amino acids. Many amino acids and amino acid esters are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y., USA).

Representative, but not limiting, amino acids suitable for use in the present invention are generally of the formula

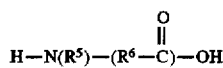

$$H-N(R^5)-(R^6-\overset{O}{\underset{\|}{C}})-OH \qquad II$$

wherein:

R$^5$ is hydrogen, C$_1$–C$_4$ alkyl, or C$_2$–C$_4$ alkenyl;

R$^6$ is C$_1$–C$_{24}$ alkyl, C$_2$–C$_{24}$ alkenyl, C$_3$–C$_{10}$ cycloalkyl, C$_3$–C$_{10}$ cycloalkenyl, phenyl, naphthyl, (C$_1$–C$_{10}$ alkyl) phenyl, (C$_2$–C$_{10}$ alkenyl) phenyl, (C$_1$–C$_{10}$ alkyl) naphthyl, (C$_2$–C$_{10}$ alkenyl) naphthyl, phenyl (C$_1$–C$_{10}$ alkyl), phenyl (C$_2$–C$_{10}$ alkenyl), naphthyl (C$_1$–C$_{10}$ alkyl), or naphthyl (C$_2$–C$_{10}$ alkenyl);

R$^6$ being optionally substituted with C$_1$–C$_4$ alkyl, C$_2$–C$_4$ alkenyl, C$_1$–C$_4$ alkoxy, —OH, —SH, —CO$_2$R$^7$, C$_3$–C$_{10}$ cycloalkyl, C$_3$–C$_{10}$ cycloalkenyl, heterocycle having 3–10 ring atoms wherein the hetero atom is one or more of N, O, S, or any combination thereof, aryl, (C$_1$–C$_{10}$ alk)aryl, ar(C$_1$–C$_{10}$ alkyl) or any combination thereof;

R$^6$ being optionally interrupted by oxygen, nitrogen, sulfur, or any combination thereof; and R$^7$ is hydrogen, C$_1$–C$_4$ alkyl, or C$_2$–C$_4$ alkenyl.

The preferred naturally occurring amino acids for use in the present invention as amino acids or components of a peptide are alanine, arginine, asparagine, aspartic acid, citrulline cysteine, cystine, glutamic acid, glutamine, glycine, histidine, isoleucine, leucine, lysine, methionine, ornithine, phenylalanine, proline, serine, threonine, tryptophan, tyrosine, valine, hydroxyproline, β-carboxyglutamic acid, γ-carboxyglutamic acid, phenylglycine, or O-phosphoserine. The most preferred amino acids are arginine, leucine, lysine, phenylalanine, tyrosine, tryptophan, valine, and phenylglycine.

The preferred non-naturally occurring amino acids for use in the present invention are β-alanine, α-amino butyric acid, γ-amino butyric acid, γ-(aminophenyl) butyric acid, α-amino isobutyric acid, ε-amino caproic acid, 7-amino heptanoic acid, β-aspartic acid, aminobenzoic acid, aminophenyl acetic acid, aminophenyl butyric acid, γ-glutamic acid, cysteine (ACM), ε-lysine, methionine sulfone, norleucine, norvaline, ornithine, d-ornithine, p-nitrophenylalanine, hydroxy proline, 1,2,3,4,-tetrahydroisoquinoline-3-carboxylic acid, and thioproline.

Poly amino acids are either peptides or two or more amino acids linked by a bond formed by other groups which can be linked, e.g., an ester or an anhydride linkage. Special mention is made of non-naturally occurring poly amino acids and particularly non-naturally occurring hetero-poly amino acids, i.e. of mixed amino acids.

Peptides are two or more amino acids joined by a peptide bond. Peptides can vary in length from di-peptides with two amino acids to polypeptides with several hundred amino acids. See, Walker, *Chambers Biological Dictionary*, Cambridge, England: Chambers Cambridge, 1989, page 215. Special mention is made of non-naturally occurring peptides and particularly non-naturally occurring peptides of mixed amino acids. Special mention is also made of di-peptides, tri-peptides, tetra-peptides, and pentapeptides, and particularly, the preferred peptides are di-peptides and tri-peptides. Peptides can be homo- or hetero- peptides and can include natural amino acids, synthetic amino acids, or any combination thereof.

Proteinoids

Proteinoids are artificial polymers of amino acids. Proteinoids preferably are prepared from mixtures of amino acids. Preferred proteinoids are condensation polymers, and most preferably, are thermal condensation polymers. These polymers may be directed or random polymers. Proteinoids can be linear, branched, or cyclical, and certain proteinoids can be units of other linear, branched, or cyclical proteinoids.

Special mention is made of diketopiperazines. Diketopiperazines are six member ring compounds. The ring includes two nitrogen atoms and is substituted at two carbons with two oxygen atoms. Preferably, the carbonyl groups are at the 2 and 5 ring positions. These rings can be optionally, and most often are, further substituted.

Diketopiperazine ring systems may be generated during thermal polymerization or condensation of amino acids or amino acid derivatives. (Gyore, J; Ecet M. *Proceedings Fourth ICTA (Thermal Analysis)*, 1974, 2, 387–394 (1974)). These six membered ring systems were presumably generated by intra-molecular cyclization of the dimer prior to further chain growth or directly from a linear peptide (Reddy, A. V., *Int. J. Peptide Protein Res.*, 40, 472–476 (1992); Mazurov, A. A. et al., *Int. J. Peptide Protein Res.*, 42, 14–19 (1993)).

Diketopiperazines can also be formed by cyclodimerization of amino acid ester derivatives as described by Katchalski et al., *J. Amer. Chem. Soc.*, 68, 879–880 (1946), by cyclization of dipeptide ester derivatives, or by thermal dehydration of amino acid derivatives and high boiling solvents as described by Kopple et al., *J. Org. Chem.*, 33 (2), 862–864 (1968).

Diketopiperazines typically are formed from α-amino acids. Preferably, the α-amino acids of which the diketopiperazines are derived are glutamic acid, aspartic acid, tyrosine, phenylalanine, and optical isomers of any of the foregoing.

Modified Amino Acids and Poly Amino Acids

Modified amino acids, poly amino acids, or peptides are either acylated or sulfonated and include amino acid amides and sulfonamides.

Acylated Amino Acids and Poly Amino Acids

Although any acylated amino acids or poly amino acids are useful in the present invention, special mention is made of acylated amino acids having the formula $$Ar^2-Y-(R^8)_n-OH \quad \text{III}$$

wherein $Ar^2$ is a substituted or unsubstituted phenyl or naphthyl; Y is $$\underset{\|}{-\overset{O}{C}-},$$

$R^8$ has the formula $$-N(R^{10})-R^9-\overset{O}{\underset{\|}{C}}-,$$

wherein:

$R^9$ is $C_1$ to $C_{24}$ alkyl, $C_1$ to $C_{24}$ alkenyl, phenyl, naphthyl, ($C_1$ to $C_{10}$ alkyl) phenyl, ($C_1$ to $C_{10}$ alkenyl) phenyl, ($C_1$ to $C_{10}$ alkyl) naphthyl, ($C_1$ to $C_{10}$ alkenyl) naphthyl, phenyl ($C_1$ to $C_{10}$ alkyl), phenyl ($C_1$ to $C_{10}$ alkenyl), naphthyl ($C_1$ to $C_{10}$ alkyl) and naphthyl ($C_1$ to $C_{10}$ alkenyl);

$R^9$ is optionally substituted with $C_1$ to $C_4$ alkyl, $C_1$ to $C_4$ alkenyl, $C_1$ to $C_4$ alkoxy, —OH, —SH and —$CO_2R^{11}$, cycloalkyl, cycloalkenyl, heterocyclic alkyl, alkaryl, heteroaryl, heteroalkaryl, or any combination thereof;

$R^{11}$ is hydrogen, $C_1$ to $C_4$ alkyl or $C_1$ to $C_4$ alkenyl;

$R^9$ is optionally interrupted by oxygen, nitrogen, sulfur or any combination thereof; and $R^{10}$ is hydrogen, $C_1$ to $C_4$ alkyl or $C_1$ to $C_4$ alkenyl.

Special mention is also made of those having the formula $$R^{12}-\overset{O}{\underset{\|}{C}}-\underset{\underset{R^{13}}{|}}{N}-(R^{14})-\overset{O}{\underset{\|}{C}}-OH \quad \text{IV}$$

wherein:

$R^{12}$ is (i) $C_3$-$C_{10}$ cycloalkyl, optionally substituted with $C_1$-$C_7$ alkyl, $C_2$-$C_7$ alkenyl, $C_1$-$C_7$ alkoxy, hydroxy, phenyl, phenoxy or —$CO_2R^{15}$, wherein $R^{15}$ is hydrogen, $C_1$-$C_4$ alkyl, or $C_2$-$C_4$ alkenyl; or (ii) $C_1$-$C_6$ alkyl substituted with $C_3$-$C_{10}$ cycloalkyl;

$R^{13}$ is hydrogen, $C_1$-$C_4$ alkyl, or $C_2$-$C_4$ alkenyl;

$R^{14}$ is $C_1$-$C_{24}$ alkyl, $C_2$-$C_{24}$ alkenyl, $C_3$-$C_{10}$ cycloalkyl, $C_3$-$C_{10}$ cycloalkenyl, phenyl, naphthyl, ($C_1$-$C_{10}$ alkyl) phenyl, ($C_2$-$C_{10}$ alkenyl) phenyl, ($C_1$-$C_{10}$ alkyl) naphthyl, ($C_2$-$C_{10}$ alkenyl) naphthyl, phenyl ($C_1$-$C_{10}$ alkyl), phenyl ($C_2$-$C_{10}$ alkenyl), naphthyl ($C_1$-$C_{10}$ alkyl) or naphthyl ($C_2$-$C_{10}$ alkenyl);

$R^{14}$ being optionally substituted with $C_1$-$C_4$ alkyl, $C_2$-$C_4$ alkenyl, $C_1$-$C_4$ alkoxy, —OH, —SH, —$CO_2R^{16}$, $C_3$-$C_{10}$ cycloalkyl, $C_3$-$C_{10}$ cycloalkenyl, heterocycle having 3–10 ring atoms wherein the hetero atom is one or more of N, O, S or any combination thereof, aryl, ($C_1$-$C_{10}$ alk)aryl, ar($C_1$-$C_{10}$ alkyl), or any combination thereof;

$R^{14}$ being optionally interrupted by oxygen, nitrogen, sulfur, or any combination thereof; and $R^{16}$ is hydrogen, $C_1$-$C_4$ alkyl, or $C_2$-$C_4$ alkenyl.

Acylated amino acids may be prepared by reacting single amino acids, mixtures of two or more amino acids, or amino acid esters with an amine modifying agent which reacts with free amino moieties present in the amino acids to form amides.

Suitable, but non-limiting, examples of acylating agents useful in preparing acylated amino acids include acid chloride acylating agents having the formula $$R^{17}-\overset{O}{\underset{\|}{C}}-X$$

wherein:

$R^{17}$ an appropriate group for the modified amino acid being prepared, such as, but not limited to, alkyl, alkenyl, cycloalkyl, or aromatic, and particularly methyl, ethyl, cyclohexyl, cyclophenyl, phenyl, or benzyl, and X is a leaving group. Typical leaving groups include, but are not limited to, halogens such as chlorine, bromine and iodine.

Examples of the acylating agents include, but are not limited to, acyl halides including, but not limited to, acetyl chloride, propyl chloride, cyclohexanoyl chloride, cyclopentanoyl chloride, and cycloheptanoyl chloride, benzoyl chloride, hippuryl chloride and the like; and anhydrides, such as acetic anhydride, propyl anhydride, cyclohexanoic anhydride, benzoic anhydride, hippuric anhydride and the like. Preferred acylating agents include benzoyl chloride, hippuryl chloride, acetyl chloride, cyclohexanoyl chloride, cyclopentanoyl chloride, and cycloheptanoyl chloride.

The amine groups can also be modified by the reaction of a carboxylic acid with coupling agents such as the carbodiimide derivatives of amino acids, particularly hydrophilic amino acids such as phenylalanine, tryptophan, and tyrosine. Further examples include dicyclohexylcarbodiimide and the like.

If the amino acid is multifunctional, i.e. has more than one —OH, —$NH_2$ or —SH group, then it may optionally be acylated at one or more functional groups to form, for example, an ester, amide, or thioester linkage.

In acylated poly amino acids, one or more of the amino acids may be modified (acylated). Modified poly amino acids may include one or more acylated amino acid(s). Although linear modified poly amino acids will generally include only one acylated amino acid, other poly amino acid configurations can include more than one acylated amino acid. Poly amino acids can be polymerized with the acylated amino acid(s) or can be acylated after polymerization.

Sulfonated Amino Acids and Poly Amino Acids

Sulfonated amino acids and poly amino acids are modified by sulfonating at least one free amine group with a sulfonating agent which reacts with at least one of the free amine groups present.

Special mention is made of compounds of the formula $$Ar^3-Y-(R^{18})_n-OH \quad \text{V}$$

wherein $Ar^3$ is a substituted or unsubstituted phenyl or naphthyl;

Y is —$SO_2$—, $R^{18}$ has the formula $$-N(R^{20})-R^{19}-\overset{O}{\underset{\|}{C}}-,$$

wherein:

$R^{19}$ is $C_1$ to $C_{24}$ alkyl, $C_1$ to $C_{24}$ alkenyl, phenyl, naphthyl, ($C_1$ to $C_{10}$ alkyl) phenyl, ($C_1$ to $C_{10}$ alkenyl) phenyl, ($C_1$ to $C_{10}$ alkyl) naphthyl, ($C_1$ to $C_{10}$ alkenyl) naphthyl, phenyl ($C_1$ to $C_{10}$ alkyl), phenyl ($C_1$ to $C_{10}$ alkenyl), naphthyl ($C_1$ to $C_{10}$ alkyl) and naphthyl ($C_1$ to $C_{10}$ alkenyl);

$R^{19}$ is optionally substituted with $C_1$ to $C_4$ alkyl, $C_1$ to $C_4$ alkenyl, $C_1$ to $C_4$ alkoxy, —OH, —SH and —$CO_2R^{21}$ or any combination thereof;

$R^{21}$ is hydrogen, $C_1$ to $C_4$ alkyl or $C_1$ to $C_4$ alkenyl;

$R^{19}$ is optionally interrupted by oxygen, nitrogen, sulfur or any combination thereof; and $R^{20}$ is hydrogen, $C_1$ to $C_4$ alkyl or $C_1$ to $C_4$ alkenyl.

Suitable, but non-limiting, examples of sulfonating agents useful in preparing sulfonated amino acids include sulfonating agents having the formula $R^{22}$—$SO_2$—X wherein $R^{22}$ is an appropriate group for the modified amino acid being prepared such as, but not limited to, alkyl, alkenyl, cycloalkyl, or aromatics and X is a leaving group as described above. One example of a sulfonating agent is benzene sulfonyl chloride.

Modified poly amino acids and peptides may include one or more sulfonated amino acid(s). Although linear modified poly amino acids and peptides used generally include only one sulfonated amino acid, other poly amino acid and peptide configurations can include more than one sulfonated amino acid. Poly amino acids and peptides can be polymerized with the sulfonated amino acid(s) or can be sulfonated after polymerization.

Proteins

Proteins are naturally occurring (i.e. not artificial) polymers of amino acids.

Enteric Coating Materials

Enteric coating materials known to those skilled in the art such as, for example, cellulose acetate trimellitate (CAT) and cellulose acetate phthalate (CAP), are suitable for use in the preservation as well.

Formation

These carriers, and particularly proteinoids, acylated amino acids or poly amino acids, sulfonated amino acids or poly amino acids, and proteins are often insoluble or relatively insoluble in neutral or mildly acidic solutions but are also soluble, as are the imidazole derivatives useful in the present invention, in aqueous acid solutions wherein the volume to volume ratio of acid to water is greater than about 3:7. Suitable aqueous acid solvents are as above, i.e. volatile organic acids, such as for example, aqueous acetic acid, aqueous formic acid, and the like. These acids will volatilize upon nebulization or can be diluted in the aqueous solution, thereby decreasing the concentration of the acid and reversing the solubility of the carrier even in the absence of a precipitator. For example, see currently filed U.S. patent application Ser. No. 08/475,882, filed on Jun. 7, 1995 (attorney's docket no. 1946/09202) entitled "SPRAY DRYING METHOD AND APPARATUS".

Microsphere formation occurs when the concentration of the acid in the carrier/active agent solution is decreased. As this solution is nebulized, the acid evaporates, decreasing the concentration of the acid in solution to less than 30% by volume. The carrier, then, will self assemble to form microspheres containing any optional active agent. The cargo must be stable in the concentrated acid for the time and conditions necessary to carry out the operation. Alternately, the carrier solution can be diluted, such as with water, whereby the acid concentration is decreased and the carrier precipitates to form microspheres. Preferably, the microspheres are prepared by spray drying.

The microspheres can be pH adapted by using base or acid soluble coatings including, but not limited to, proteinoid coatings, enteric coatings, acylated amino acid coatings, and the like.

Any of the solutions above may optionally contain additives such as stabilizing additives. The presence of such additives promotes the stability and dispersability of the active agent in solution. The stabilizing additives may be employed at a concentration ranging between about 0.1 and 5% (w/v), preferably about 0.5% (w/v). Suitable, but non-limiting examples of stabilizing additives include buffer salts, gum acacia, gelatin, methyl cellulose, polyethylene glycol, and polylysine.

The amount of active agent that may be incorporated in the microsphere is dependent upon a number of factors which include the concentration of active agent in the solution as well as the affinity of the active agent for the carrier. The concentration of the active agent in the final formulation also will vary depending on the required amounts for any particular end use. When necessary, the exact concentration can be determined by, for example, reverse phase HPLC analysis.

The microspheres and, therefore, the solutions described above may also include one or more enzyme inhibitors. Such enzyme inhibitors include, but are not limited to, compounds such as actinonin or epiactinonin and derivatives thereof.

The microspheres are particularly useful for administering itraconazole derivatives to any animals, including but not limited to, birds and mammals, such as primates and particularly humans; and insects. These microsphere systems are particularly advantageous for delivering these active agents as the active agent would otherwise be destroyed or rendered less effective by conditions encountered before the microsphere reaches the active agent target zone (i.e., the area in which the active agent of the delivery composition are to be released) and within the body of the animal to which they are administered. Furthermore, these microspheres can deliver relatively high amounts of the imidazole derivative and retain a high bioavailability.

DESCRIPTION OF THE PREFERRED EMBODIMENTS

The following examples illustrate the present invention without limitation.

EXAMPLE 1

Solubilization of Itraconazole

Acetic acid solutions were prepared in water to 10%, 20%, 50% and 75% concentrations (expressed as volume glacial acetic acid/total volume of solution×100). 100 mg itraconazole solute were then mixed independently with 1 ml of each solution and visually monitored for dissolution. If necessary, additional 1 ml aliquots of each acetic acid solution were added until the itraconazole solute was dissolved.

Results are illustrated in Table 1 below. The solubilized material did not precipitate readily.

TABLE 1

| Concentration of Acid in Solvent | SOLUBILITY Amount of Solvent | | | | | | | |
|---|---|---|---|---|---|---|---|---|
| | 1 ml Cold | 1 ml Hot | 2 ml Cold | 2 ml Hot | 3 ml Cold | 3 ml Hot | 4 ml Cold | 4 ml Hot |
| 10% Acetic Acid v:v | Ins. | Ins. | Ins. | Ins. | Ins. | Ins. | — | Ins. |
| 20% Acetic Acid v:v | Ins. | Ins. | Ins. | Ins. | Ins. | Part Sol. | — | — |
| 50% Acetic Acid v:v | Ins. | Ins. | Ins. | Sol. | Ins. | — | — | — |
| 75% Acetic Acid v:v | Sol. | — | — | — | — | — | — | — |

EXAMPLE 2

Solubilization of Itraconazole 100 mg of itraconazole solute were dissolved in 1 ml glacial acetic acid solvent and aqueous acetic acid solvent at various concentrations. Results are illustrated in Table 2 below.

TABLE 2

ITRACONAZOLE SOLUTE

| % Acetic Acid (v:v) | Dissolved Itraconazole % |
|---|---|
| 100 | >33 (dissolves freely on addition) |
| 75 | >10 (dissolves freely on addition) |
| 40 | 5 (diss. conc. acid, then dilute) |
| 20 | 2.5 (diss. conc. acid, then dilute) |

EXAMPLE 3

Preparation of Itraconazole-Containing Microspheres One-Solution Method 60 grams of itraconazole solute (Janssen Pharmaceutica) were added to 1.43 liters of glacial acetic acid solvent, and the mixture was stirred to dissolve the solute. 1.43 liters of water were then added using a pump at a flow rate of 25 ml/min. Slight clouding of the solution was observed, but cleared upon further stirring. 166 grams of proteinoid (Glu-Asp-Tyr-Phe-Orn) were added and dissolved with further stirring. The final solution was filtered through folded tissue paper.

Using peristaltic pumps, the solution was fed through a Virtis SD04 spray drying apparatus under the conditions of Table 3 below.

TABLE 3

SPRAY DRYING CONDITIONS

| Solution flow rate | 7–8 ml/min |
|---|---|
| Inlet temperature | 175° C. |
| Outlet temperature | 116° C. |
| Blower speed | full |
| Compressor pressure | full |

Stable proteinoid microspheres containing itraconazole were formed. Analysis of typical microspheres using RP-HPLC demonstrated that they contained 14–21% itraconazole by weight.

Figure 1A:
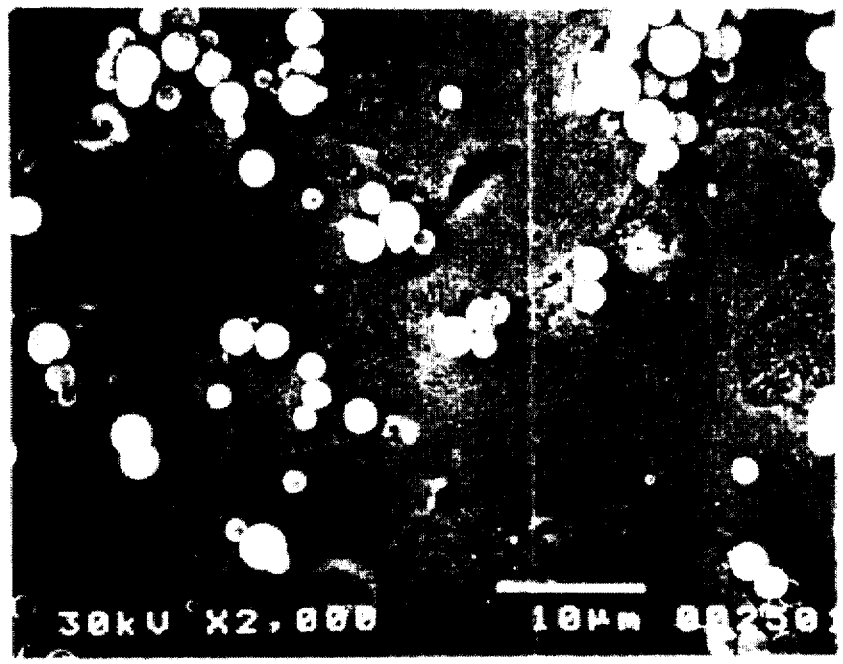
Figure 1B:
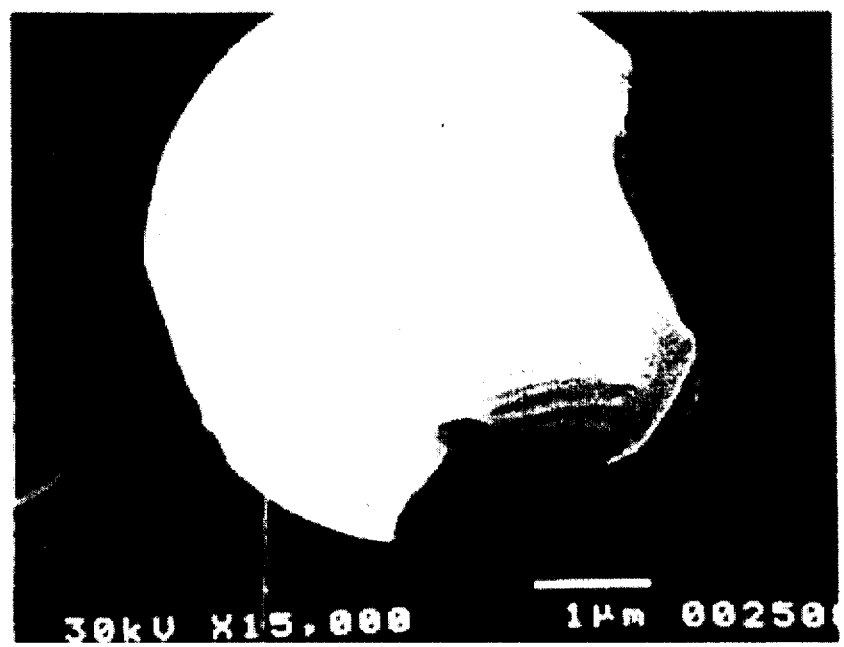
Figure 1G:
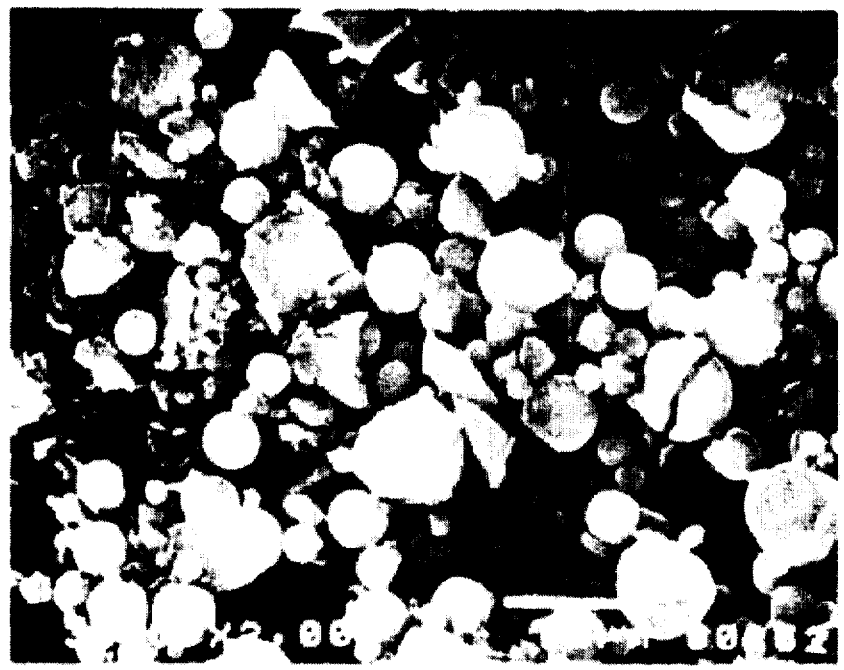
Figure 1H:
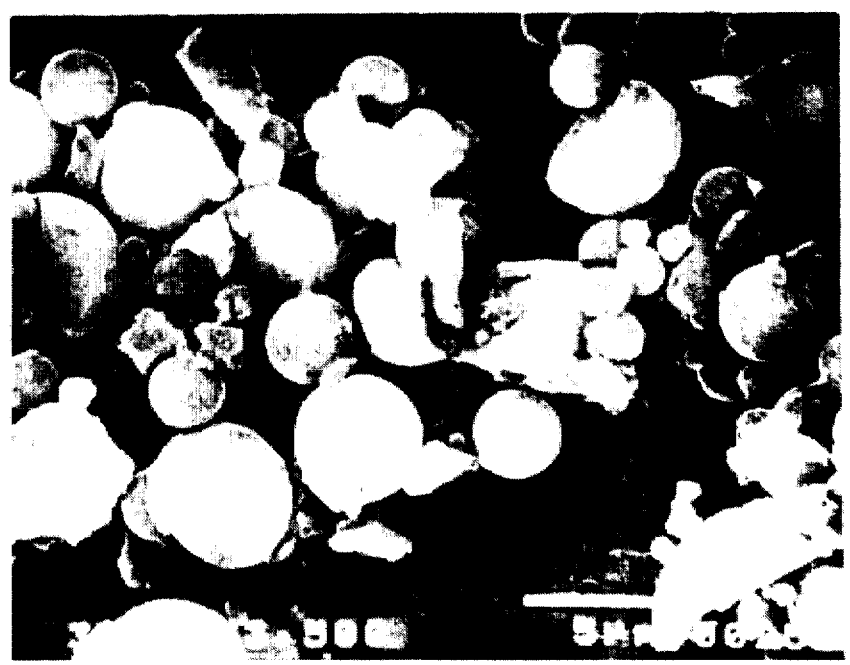

Scanning electron microscopy in FIGS. 1A–1H illustrates that the microspheres were smooth and spherical and had diameters ranging from 0.1 µm to about 5 µm. When mechanically crushed only the larger spheres shattered, while the smaller spheres remained intact. Crushing revealed a solid internal structure. See, FIG. 1G and 1H.

All patents, applications, publications, and test methods mentioned herein are hereby incorporated by reference in their entirety.

Many variations of the present invention will suggest themselves to those skilled in the art in light of the above-detailed description in which obvious variations are within the full intended scope of the appended claims.

What is claimed is:

1. A microsphere comprising (a) a solubilized imidazole derivative active agent comprising an imidazole derivative having the formula $$R^4 \underset{}{\overset{}{\fbox{}}} \begin{array}{c} N \\ \| \\ N \end{array} - R^3 \qquad I$$

$$R^1 - \underset{R^2}{\overset{R}{\underset{|}{C}}} - \underset{Ar}{\overset{|}{C}} - O - (CH_2)_n - Ar^1$$

wherein R, $R^1$, and $R^2$ are independently hydrogen or lower alkyl;

$R^3$ is hydrogen, methyl or ethyl;

$R^4$ is hydrogen or methyl

Ar is phenyl, monohalophenyl, dihalophenyl, trihalophenyl, mono(lower alkyl)phenyl, di(lower alkyl)phenyl, lower alkoxyphenyl, or halothienyl;

$Ar^1$ is phenyl, monohalophenyl, dihalophenyl, trihalophenyl, mono(lower alkyl)phenyl, di(lower alkyl)phenyl, lower alkoxyphenyl, or cyanophenyl; and n is 1 or 2; and a solvent, wherein the solution comprises from about 3 to about 40 percent by weight of solute and from about 60 to about 97 parts by weight of solvent based upon 100 parts by weight of solution; and (b) a microsphere forming carrier selected from the group consisting of (i) a proteinoid of mixed amino acids;

(ii) an acylated amino acid or poly amino acid or a salt thereof;

(iii) a sulfonated amino acid or poly amino acid or a salt thereof;

(iv) a protein or a salt thereof; and (v) any combination thereof.

2. A microsphere as defined in claim 1, wherein said solubilized imidazole derivative active agent comprises solubilized itraconazole.

3. A method for administering an imidazole derivative active agent to an animal in need of such treatment, such method comprising (A) preparing a microsphere as defined in claim 1, and (B) orally administering said microsphere to said animal.

4. A method for treating a fungal infection in an animal in need of such treatment, said method comprising administering to said animal a therapeutically effective amount of a microsphere as defined in claim 1.

\* \* \* \* \*